(12) United States Patent
Le Roy-Delage et al.

(10) Patent No.: US 8,236,100 B2
(45) Date of Patent: Aug. 7, 2012

(54) METHOD OF CHARACTERIZING THE SELF-HEALING PROPERTIES OF A SET CEMENT BASED MATERIAL IN CONTACT WITH HYDROCARBONS

(75) Inventors: Sylvaine Le Roy-Delage, Paris (FR); Hélène Bulté-Loyer, Sceaux (FR); Bernard Dargaud, Elancourt (FR); Hélène Heurdier, Montrouge (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 140 days.

(21) Appl. No.: 12/913,761

(22) Filed: Oct. 28, 2010

(65) Prior Publication Data

US 2011/0107848 A1     May 12, 2011

(30) Foreign Application Priority Data

Nov. 6, 2009 (EP) .................................. 09290853

(51) Int. Cl.
*C04B 14/00* (2006.01)
*E21B 33/13* (2006.01)
(52) U.S. Cl. ................. 106/724; 166/292; 166/293
(58) Field of Classification Search .......... 106/724; 166/292, 293
See application file for complete search history.

(56) References Cited

U.S. PATENT DOCUMENTS

| | | | | |
|---|---|---|---|---|
| 7,373,991 B2 * | 5/2008 | Vaidya et al. | ................ | 166/381 |
| 2011/0120715 A1 * | 5/2011 | Le Roy-Delage et al. | .... | 166/292 |

FOREIGN PATENT DOCUMENTS

WO    2009015725    2/2009

OTHER PUBLICATIONS

Roth, Talisman Energy, C. Reeves, C.R. Johnson, G. De Bruijn, M. Bellabarba, S. Le Roy-Delage, H.Bulte Loyer Innovative Hydraulic Isolation Material Preserves Well Integrity IADC/SPE 112715 Drilling Conference to be held in Orlando Mar. 2008.

N. Moroni, Eni, N. Panciera, Stogit, C. Johnson, S. LeRoy-Delage, H. Bulte-Loyer, S. Cantini, E. Bellegia and R. Illuminati Overcoming the Weak Link in Cemented Hydraulic Isolation SPE 110523 ATCE, Anaheim., Nov. 2007.

S. Cantini; E. Belleggia; R. Illuminati C. Johnson, S. Le Roy-Delage, H. Bulte-Loyer An Integrated Approach to Achieve Optimal Zonal Isolation Paper presented at Schlumberger Reservoir Symposium held in Beijing Oct. 2007.

(Continued)

*Primary Examiner* — Jewel V Thompson
(74) *Attorney, Agent, or Firm* — Matthias Abrell (57) ABSTRACT

Methods of characterizing the self-healing properties of a set cement based material in contact with hydrocarbons in an oil- and/or gas-well are described. The methods comprise: providing a test cell (10); providing said test cell (10) with a sample (31, 40) of the set cement based material; damaging the sample to simulate a loss of zonal isolation resulting from damages made to the set cement based material in the oil- or gas-well; injecting a hydrocarbon fluid in the test cell; allowing the cement based material to heal by itself; measuring the differential pressure ($\Delta P$) across the sample (31, 40); and characterizing the self-healing properties of the cement based material from the measure of said differential pressure ($\Delta P$).

20 Claims, 4 Drawing Sheets

OTHER PUBLICATIONS

C. Johnson, S. Le Roy-Delage and H. Bulte-Loyer Managing Zonal Isolation Risk Through Use of a New Responsive Cement Material DOT (Deep Offshore Technology Conference), Stavanger, Norway, Oct. 10-12, 2007.

Johnson C. R. Bulte H., Le Roy-Delage S., Illuminati R. , Belleggia E., Moroni N., Barbieri E., Self Healing Cement—Novel Technology to Achieve Leak-Free UGS Wells, Communication during SPE Applied Technology Workshop Underground storage of natural gas-today and tomorrow held in Krakow, Poland, May 28-31, 2007.

P. Cavanagh, Suncor Energy Inc, C.R. Johnson, S. Le Roy-Delage, G. DeBruijn, I. Cooper, D. Guillot, H. Bulte, B. Dargaud, Schlumberger Self-Healing Cement—Novel Technology to Achieve Leak-Free Wells SPE/IADC 105781 Drilling Conference Amsterdam, Feb. 2007.

* cited by examiner

METHOD OF CHARACTERIZING THE SELF-HEALING PROPERTIES OF A SET CEMENT BASED MATERIAL IN CONTACT WITH HYDROCARBONS

FIELD OF THE INVENTION

The invention relates to methods of characterizing the self-healing properties of a set cement based material in contact with hydrocarbons in an oil- and/or gas-well.

BACKGROUND OF THE INVENTION

Numerous oil and/or gas wells present zonal isolation issues. For example, such issues may be in the form of a sustained casing pressure, or similar unwanted hydrocarbon migration issues.

In order to improve long-term zonal isolation, new cement based material having self-healing properties have been developed. Hydrocarbons activate the self-healing blend material whenever the integrity of the cement sheath is compromised by cracks, fissures, or by a micro-annulus. Leakage paths are then sealed thanks to a swelling mechanism.

Self-healing cements (SHCs) are responsive materials. This means that they self-repair. Self-repairing is initiated when a hydrocarbon fluid originating from the formation comes into contact with an exposed surface of the SHC material where, when and if it is needed.

Hence, the self-healing property of cement based materials offers technological solutions to the increasing environmental challenges that the oil and gas industry are currently facing.

Self-healing property was described in the following SPE papers, all of which are incorporated herein in their entireties:

Roth, Talisman Energy, C. Reeves, C. R. Johnson, G. De Bruijn, M. Bellabarba, S. Le Roy-Delage, H. Bulte Loyer, Innovative Hydraulic Isolation Material Preserves Well Integrity IADC/SPE 112715 Drilling Conference held in Orlando, March 2008;

N. Moroni, Eni, N. Panciera, Stogit, C. Johnson, S. LeRoy-Delage, H. Bulte-Loyer, S. Cantini, E. Bellegia and R. Illuminati Overcoming the Weak Link in Cemented Hydraulic Isolation SPE 110523 ATCE, Anaheim., November 2007;

S. Cantini; E. Belleggia; R. Illuminati C. Johnson, S. Le Roy-Delage, H. Bulte-Loyer, An Integrated Approach to Achieve Optimal Zonal Isolation Paper presented at Schlumberger Reservoir Symposium held in Beijing, October 2007;

C. Johnson, S. Le Roy-Delage and H. Bulte-Loyer Managing Zonal Isolation Risk Through Use of a New Responsive Cement Material DOT (Deep Offshore Technology Conference), Stavanger, Norway, Oct. 10-12 2007;

Johnson C. R. Bulte H., Le Roy-Delage S., Illuminati R., Belleggia E., Moroni N., Barbieri E., Self Healing Cement-Novel Technology to Achieve Leak-Free UGS Wells, Communication during SPE Applied Technology Workshop Underground storage of natural gas-today and tomorrow" held in Krakow, Poland, 28-31 May 2007; and P. Cavanagh, Suncor Energy Inc, C. R. Johnson, S. Le Roy-Delage, G. DeBruijn, I. Cooper, D. Guillot, H. Bulte, B. Dargaud, Schlumberger Self-Healing Cement—Novel Technology to Achieve Leak-Free Wells, SPE/IADC 105781 Drilling Conference Amsterdam, February 2007.

However, the self-healing property are currently difficult to characterize as neither the ASTM (American Society for Testing and Materials), API (American Petroleum Institute) nor ISO (International Organization for Standardization) standards are describing any methodology. These "normalization entities" do not provide any recommendations to characterize this property.

SUMMARY

Therefore, and as long term zonal isolation provided by these cement based materials is very important and challenging to achieve, there is a need to define a measure of the self-healing properties of cements.

Accordingly, some embodiments aim at generating, or simulating, the situation encountered in an oil- and/or gas-well when the isolation provided by the cement is lost, and at evaluating the efficiency of SHCs to restore the original isolation, the simulated loss of isolation in the well being either due to a failure of the cement itself—cracks, fissures—, or the creation of a micro-annulus between the casing and the cement, or between the cement and formation.

Some embodiments provide methods of characterizing the self-healing properties of a set cement based material in contact with hydrocarbons in an oil- or gas-well. More particularly, embodiments provide such methods for quantifying self-healing properties of a responsive cement based material in contact with gaseous hydrocarbons. Any cement or cementitious material can be tested according to the present invention.

Some embodiments concern methods of characterizing the self-healing properties of a set cement based material in contact with hydrocarbons in an oil- or gas-well, comprising:
  providing a test cell;
  providing said test cell with a sample of the set cement based material;
  damaging the sample to simulate a loss of zonal isolation resulting from damages made to the set cement based material in the oil- or gas-well;
  injecting a hydrocarbon fluid at a constant flow rate in the test cell;
  allowing the cement based material to heal by itself;
  measuring the differential pressure across the sample; and
  characterizing the self-healing properties of the cement based material from the measure of said differential pressure.

Preferentially, —the damages made to the cement based material sample comprise a micro-annulus; —a slurry of the cement based material is poured inside the test cell, and the cement based material is allowed to shrink under drying in order to create the micro-annulus between an internal wall of the test cell and the cement based material sample; —the hydrocarbon fluid is preferably a hydrocarbon gas injected in the test cell, and flowing in the micro-annulus between the internal wall of the test cell and the cement based material sample; —the damages made to the cement based material sample comprise cracks and/or fissures; —the cement based material sample is fractured substantially along its longitudinal axis, the resulting cracks or fissures dividing the sample in two parts; —the hydrocarbon fluid is preferably a hydrocarbon gas injected in the test cell, and flowing in said cracks or fissures; —the test cell is a substantially cylindrical metallic cell; —the hydrocarbon fluid is injected in the test cell at a constant flow rate; —the method further comprises a step of measuring initial conductivity of the damaged sample to a gas flow preferably using a non-reactive gas; —the non-reactive gas is preferably nitrogen; —the evolution of the differential pressure $\Delta P$ is monitored; and —if the differential pressure $\Delta P$ increases, this is an indication that the micro-annulus or crack/fissure size has reduced and that the set cement system has reacted with the gas and shows self-healing properties. In a preferred embodiment, the fluid is close to a "reservoir"

fluid based on a mixture of hydrocarbon fluid carbon dioxide and hydrogen sulfide at various proportion.

BRIEF DESCRIPTION OF THE DRAWINGS

Other features and aspects will be apparent from the following description and the accompanying drawings, in which.

DETAILED DESCRIPTION

At the outset, it should be noted that in the development of any such actual embodiment, numerous implementation-specific decisions must be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In the summary and this detailed description, each numerical value should be read once as modified by the term "about" (unless already expressly so modified), and then read again as not so modified unless otherwise indicated in context.

Methods of characterizing the self-healing properties of a set cement based material in contact with hydrocarbons in an oil- and/or gas-well, comprises a step of providing a test cell.

Figure 1:
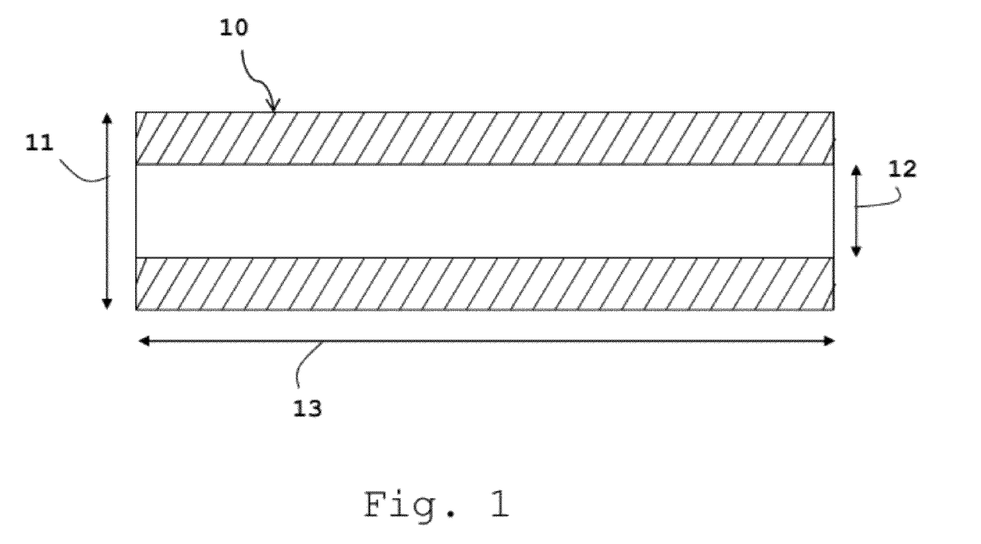
FIG. 1 is a section view of a test cell for the implementation of the method according to the invention.

The test cell is a the sample test cell. As shown in FIG. 1, the test cell 10 is substantially cylindrical. The cylinder is preferably metallic. For example, a metallic cylinder may be made of stainless steel. The outside diameter 11 of the cylinder is, according to a particular embodiment of the invention, 38.1 mm. Its inside diameter 12 is 21.2 mm, and its length 13 is 180 mm. The internal average roughness of the inner wall of the cylinder is set to Ra=1.6. It has to be noted that the different diameters being internal or external might vary depending on the simulation that a skilled person wants to run, the same applies to the internal average roughness.

Figure 2:
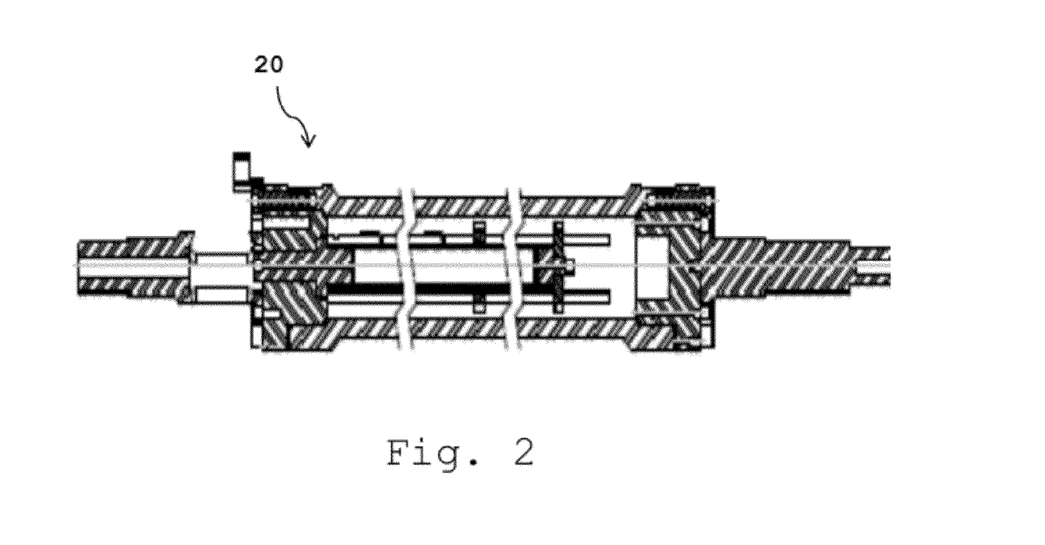
FIG. 2 is a section view of a core holder in which is placed a test cell according to the invention.

The test cell is positioned inside a core holder 20. An example of a core holder is shown in FIG. 2. This core holder is a core flood system preferentially based on a Hassler sleeve type core holder, which uses samples of 38.1 mm diameter. Core holders based on Hassler sleeve type core holders are known from the man skilled in the art.

The delivery of fluids in the test cell is performed by two volumetric pumps. The capacity of each of these pumps is, for example, of 0-16 ml/min, providing a maximum total flow rate of 32 ml/min, when the two volumetric pumps are running together. An accurate back pressure regulator maintains a constant pressure at the outlet face of the cement based material sample, when such the test cell is provided with said sample. Only one pump may be envisaged and more than two pumps could also be used depending on the simulation the skilled person wants to run.

The whole system is preferably computer controlled. All relevant measurements such as pressures, flow rates, or the temperature, can thus be monitored throughout the test.

Prior to providing the test cell with a cement based material sample, the setup of the system is tested using for example a capillary assembly that simulates the presence of the cement based material sample. The proper functioning of both the differential pressure measurement system and the back pressure regulator is assessed. This test also permits to validate the flow calculations equations under high pressure with nitrogen.

Then, the test cell is provided with the sample of a set cement based material. The set cement based material shall be damaged: either a micro-annulus is created between the core of the cement based material and the test cell or the core is fractured along its longitudinal axis, as in a Brazilian test.

A hydrocarbon fluid, for example a hydrocarbon reservoir gas, is then injected under high static pressure through the test cell containing the core of the damaged set cement. During the flow test, this gas is injected at a constant flow rate. For example, a gas composition is provided in Table 1 below. However, any type of gas can be used as long as the material to be tested reacts/swells in contact with the selected gas.

TABLE 1 gas composition

| Composition % mol | Gas A |
|---|---|
| C1 | 83 |
| N2 | 0.67 |
| CO2 | 0.3 |
| C2 | 11.36 |
| C3 | 3.8 |
| iC4 | 0.35 |
| nC4 | 0.36 |
| C5 | 0.03 |
| iC5 | 0.06 |
| nC5 | 0.05 |
| nC6 | 0.02 |

The resulting differential pressure across the sample is measured. As demonstrated in the calculations in Example 1 hereunder, this differential pressure value is directly related to the size of the micro-annulus. It is similar if the damages made to the sample consists in a fracture.

Finally, the self-healing property of the cement based material is characterized from the above measures of differential pressure across the sample. Practically, if, during the test, the differential pressure $\Delta P$ increases, this is the indication that the micro-annulus or crack size has reduced and that the set cement system has reacted with the gas.

Example 1

Tests with Gas at a High Pressure in an Annular Configuration

A cement slurry is placed in a test cell 10 comprising a metallic cylinder made of stainless steel. The cement is allowed to set. Hence, during the setting phase, the cement is let dry and is expected to shrink and to form a micro-annulus.

Figure 3:
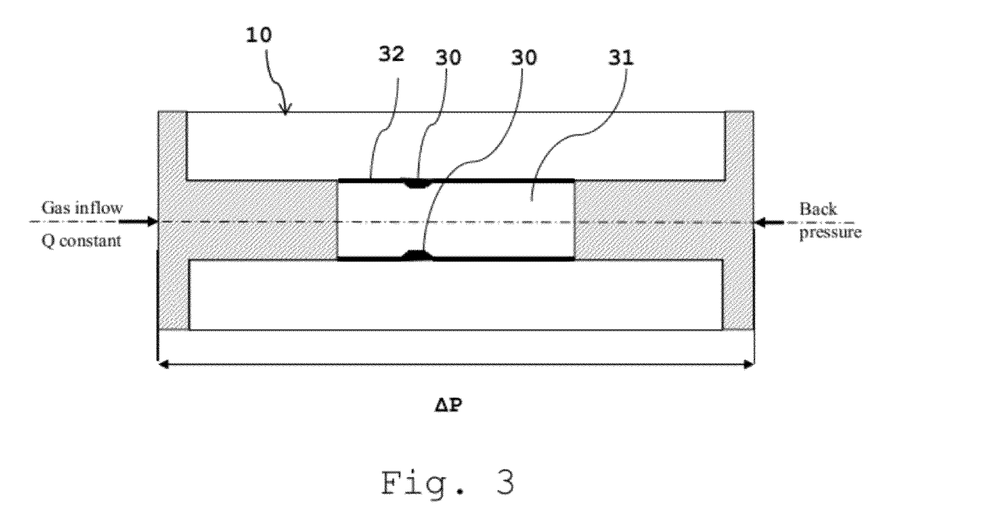
FIG. 3 is a section view of a test cell provided with a sample of a set cement, wherein a micro-annulus is created between the inside wall of the cell and the outside surface of the cement sample.

As shown in FIG. 3, two pins 30 inside the metallic cylinder ensure that the shrinked core of the set cement based material sample 31 does not slide along the core holder. After one week of curing at a selected temperature, the size of the micro-annulus 32, if such a micro-annulus is present, is determined by injecting nitrogen at pressure through the cell and by measuring the flow rate. Curing continues until a stable micro-annulus in the range of for instance 15-25 microns is obtained.

The test procedure is then achieved. The flow test conditions are as follows:

Temperature: for instance from ambient temperature up to 140° C. can be adjusted to the selected downhole conditions Injection pressure: 20.7-20.8 MPa (limited by the range of the differential pressure transducer), Back pressure: 20.7 MPa, maintained as constant as possible, Flow rate: 0-32 ml/min (rate of gas at injection pressure conditions).

The procedure of test explained below was established.

For the initial nitrogen conductivity measurement: a flow rate is used as high as the pumps and the differential pressure ($\Delta P$) measurement allow (with at least two different flow rates with meaningful $\Delta P$ values).

When switching to the hydrocarbon gas, the initial flow rate is identical to the nitrogen flow rate used previously. The $\Delta P$ evolution is monitored carefully in order to reduce flow rate if necessary. This is important because it provides indications of how fast the system reacts (with meaningful $\Delta P$ values).

The flow rate can be then reduced in order to allow a running for about 12 hours.

After that, the flow rate is increased (with gas) to a maximum in order to obtain meaningful differential pressure values. It is important that this step is properly implemented before performing the final nitrogen conductivity measurement to get better accuracy on measurement. Hence, this measurement requires meaningful $\Delta P$ values and therefore $\Delta P$ values obtained at the highest flow rates.

Some of the systems may react slowly or only to a limited extent, but still show some reaction. This information is important because it allows distinguishing between systems that do not react at all and systems that react a little. Systems that react only to a limited extent can still be improved or optimized in order to increase their reactivity.

The final N2 conductivity measurement is performed (with at least two different flow rates with meaningful $\Delta P$ values). Systematically, the measurements are carried out at different flow rates with the gas (like what is done with Nitrogen), at the beginning of the injection of gas, and at the end, just before injecting Nitrogen.

In order to calculate the micro-annulus size from the flow test data, the following assumptions were made:
- the gas flows through a homogeneous micro-annulus (unfissured sample);
- it is assumed that the test conditions are achieved under isothermal conditions;
- "minor losses" are not considered (pressure drop due to valves, fittings, elbows, bends, expansions, contractions;
- the gas flow is fully developed; and
- the gas flow takes place between smooth surfaces.

The calculations are based on the equations presented hereunder. These equations are known form the man skilled in the art.

For a Laminar Flow in thin concentric annular passage of area $2\pi RY$:

$$\left(R_e = \frac{\dot{m}}{\pi R \mu(p, T)} < 2000\right)$$

wherein Re is Reynold's number; $\dot{m}$ is the mass flow of gas, R is radius of thin concentric annular passage, $\mu$ is viscosity of gas, P is pressure, T is temperature.

For fully developed laminar flow between two parallel plates:

$$\dot{m} = \frac{\pi R \rho(p, T)}{6 \mu(p, T)} \frac{dp}{dx} Y^3$$

wherein $\rho$ is gas density and Y is the thickness of annular passage.

An estimate for Y can be obtained assuming linear variation of properties and constant pressure gradient along passage, i.e.:

$$Y = \left[\frac{6(\mu_1 + \mu_2)}{\pi R(\rho_1 + \rho_2)} \frac{(x_2 - x_1)}{(p_2 - p_1)} \dot{m}\right]^{1/3}$$

The conditions at entry is denoted by subscript 1 and at outlet denoted by subscript 2.

Gas properties under pressure (density and viscosity) have been determined by using the software "REFPROP" (Reference Fluid Thermodynamic and Transport Properties) from the National Institute of Standards and Technology (NIST).

Example 2

Tests with Gas at a High Pressure in a Crack

Figure 4:
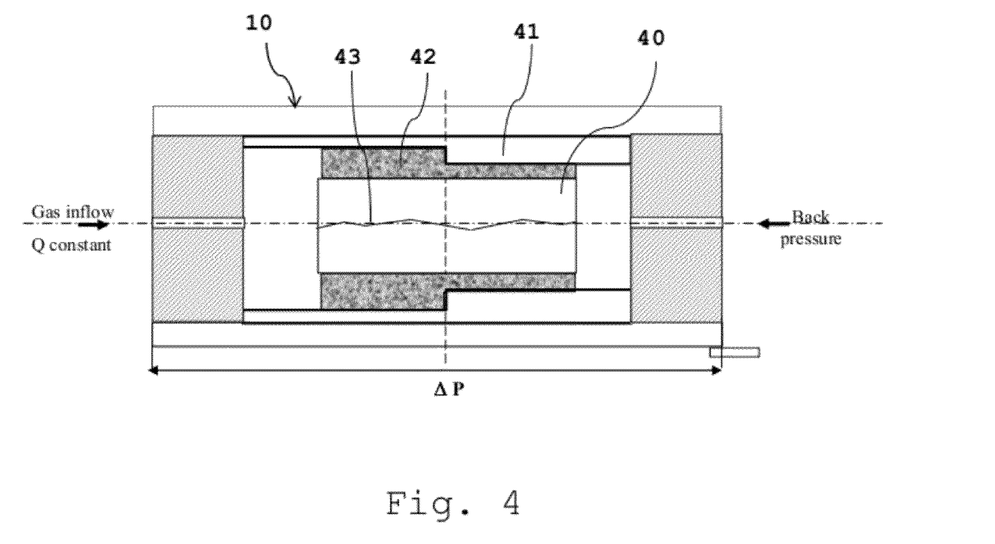
FIG. 4 is a section view of a test cell provided with a sample of a fractured set cement.

As shown in FIG. 4, the test cell 10 contains a cement sample 40 held in a thick metallic cylinder 41, the whole assembly being inserted in the Core Flood system. The thick metallic cylinder 41 is machined with an internal stop so that the core of cement cannot be extracted when gas flows through the system. The core is maintained by a thin layer of surrounding cement 42.

The cylindrical core of cement is first fractured 43 along the longitudinal axis like in a Brazilian test.

The flow test conditions are as follows:
temperature: for instance from ambient up to 140° C., can be adjusted to the selected downhole conditions;
injection pressure: 20.7-20.8 MPa (limited by the range of the differential pressure transducer, 0-20 psi),
back pressure: 20.7 MPa (maintained as constant as possible),
flow rate: 0-32 ml/min (rate of gas at injection pressure conditions).

For the initial nitrogen conductivity measurement, a flow rate is used as high as the pumps and the differential pressure ($\Delta P$) measurement allow (with at least two different flow rates with meaningful $\Delta P$ values).

When switching to the hydrocarbon gas, the initial flow rate is identical to the nitrogen flow rate used previously. The $\Delta P$ evolution is monitored carefully in order to reduce flow rate if necessary. This is important because it provides indications of how fast the system reacts (with meaningful $\Delta P$ values).

The flow rate can be then reduced in order to allow a running for about 12 hours.

After that, the flow rate is increased (with gas) to a maximum in order to obtain meaningful differential pressure values. It is important that this step is properly followed before performing the final nitrogen conductivity measurement to get better accuracy on measurement. Such measurement requires meaningful ΔP values and therefore ΔP values obtained at the highest flow rates.

Some of the systems may react slowly or only to a limited extent, but still show some reaction. This information is very important because it allows distinguishing between systems that do not react at all and systems that react a little. Systems that react only to a limited extent can still be improved or optimized to increase their reactivity.

Figure 5:
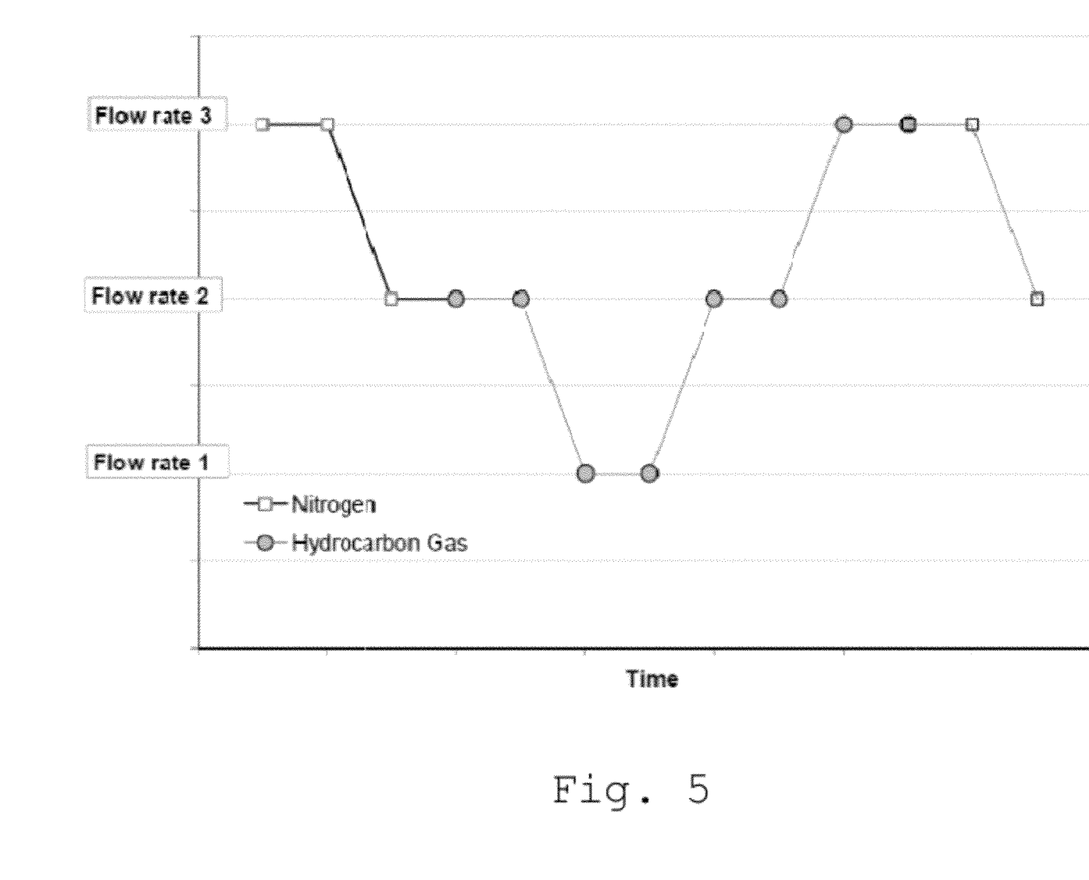
FIG. 5 is a schematic representation of the various steps that are implemented for testing the reactivity of a cement system to a hydrocarbon gas.

The final N2 conductivity measurement is performed (with at least two different flow rates with meaningful ΔP values). Systematically, the measurements are carried out at different flow rates with the gas (like what is done with Nitrogen), at the beginning of the injection of gas, and at the end, just before injecting Nitrogen. FIG. 5 illustrates the different flow rates for a typical test.

Example 3

Test Results

Figure 6:
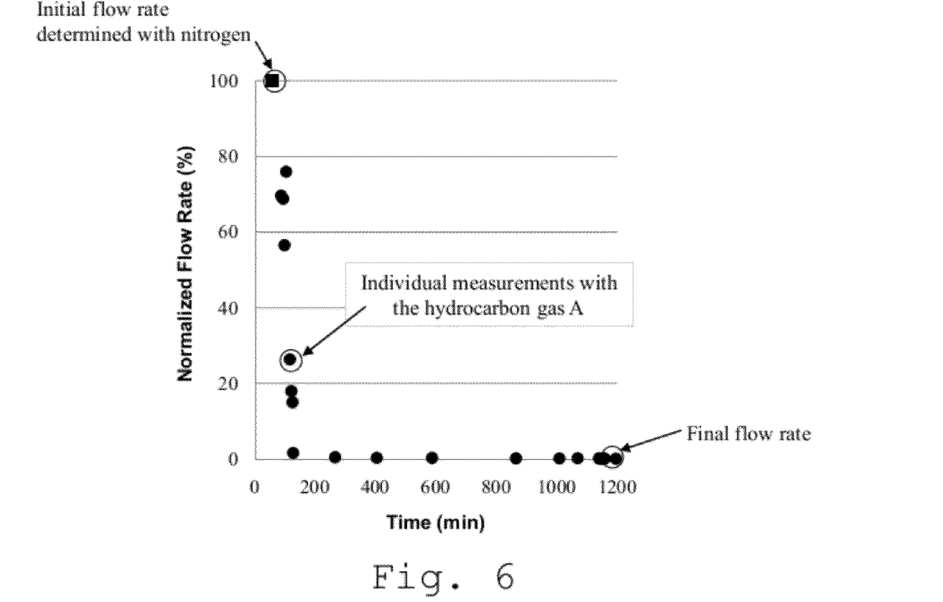
FIG. 6 illustrates the results that are obtained according to the invention, when testing a reactive cement based material, when said material is provided with a micro-annulus.
Figure 7:
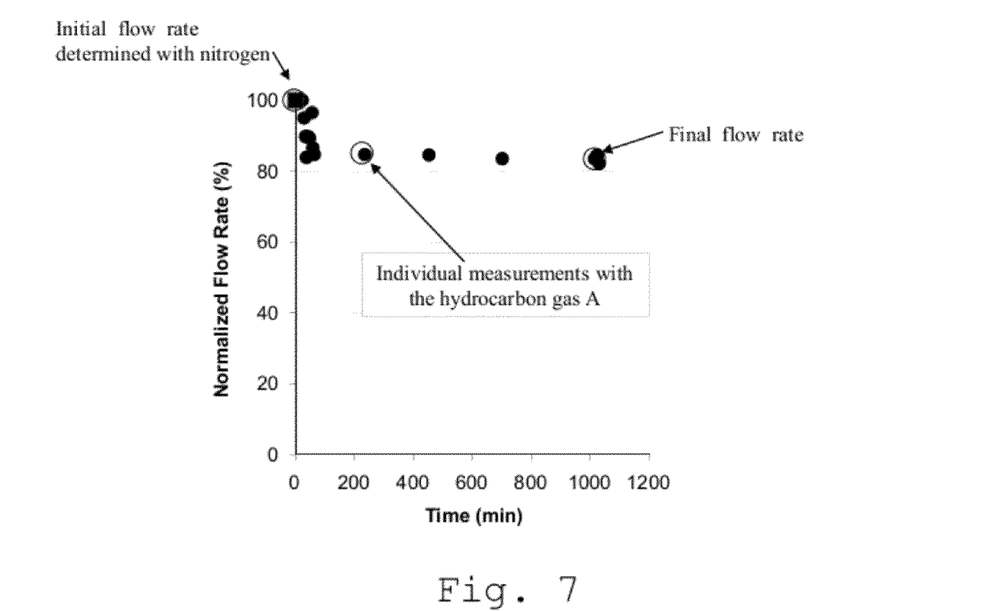
FIG. 7 illustrates the results that are obtained according to the invention, when testing a reactive cement based material, when said material is fractured.

Test results for cement based materials reacting with a hydrocarbon gas are illustrated in the graphs of FIGS. 6 and 7. These graphs display the evolution of the normalized flow rate versus time. They display the evolution of the normalized flow rate—under the high pressure conditions—during the different phases of the test with nitrogen, and, then, with the reservoir gas noted Gas A in FIGS. 6 and 7. The graph of FIG. 6 is typical of a reactive cement based material. The graph of FIG. 7 is typical of a less reactive system. As appearing in FIG. 6, the normalized gas flow rate for a reactive cement based material decreases to a value inferior to 20% in less 100 min. As appearing in FIG. 7, the normalized gas flow rate for a less reactive cement remains still greater than 80% after 1 000 min.

While preferred embodiments of the invention have been shown and described, modifications thereof can be made by one skilled in the art without departing from the spirit and teachings of the invention. Accordingly, the scope of protection is not limited by the description set out above but includes all equivalents of the subject matter of the claims.

Brazilian Test Procedure:

Brazilian test is described in Well Cementing Second Edition Editors Erik Nelson, D Guillot page Section B-6.3.3 page 650. Brazilian test is standardized for determining the tensile strength of concrete in ASTM C496 "Standard Test Method for Splitting Tensile Strength of Cylindrical Concrete Specimens".

A typical procedure for conducting Brazilian test as cited in the present disclosure is presented here under:
   Cut a cylinder core plug with for instance 1.5 inch (0.038 m) in diameter and 1 inch (0.025 m) in length. Too
   Lying the sample on its side on the test equipment.
   Increase pressure until sample failed.

The invention claimed is:

1. A method of characterizing the self-healing properties of a set cement based material in contact with hydrocarbons in an oil or gas well or both, comprising:
   providing a test cell;
   providing said test cell with a sample of the set cement based material;
   damaging the sample to simulate a loss of zonal isolation resulting from damages made to the set cement based material in the oil- or gas-well;
   injecting a hydrocarbon fluid in the test cell;
   allowing the cement based material to heal by itself;
   measuring the differential pressure (ΔP) across the sample; and
   characterizing the self-healing properties of the cement based material from the measure of said differential pressure (ΔP).

2. The method of claim 1, wherein the damages made to the cement based material sample comprise a micro-annulus.

3. The method of claim 2, wherein a slurry of the cement based material is poured inside the test cell, and the cement based material is allowed to shrink under drying in order to create the micro-annulus between an internal wall of the test cell and the cement based material sample.

4. The method of claim 2, wherein the hydrocarbon fluid is a hydrocarbon gas injected in the test cell, and flowing in the micro-annulus between the internal wall of the test cell and the cement based material sample.

5. The method of claim 1, wherein the damages made to the cement based material sample comprise cracks or fissures or both.

6. The method of claim 5, wherein the cement based material sample is fractured substantially along its longitudinal axis, the resulting cracks or fissures dividing the sample in two parts.

7. The method of claim 5, wherein the hydrocarbon fluid is a hydrocarbon gas injected in the test cell, and flowing in said cracks or fissures.

8. The method of claim 1, wherein the test cell is a substantially cylindrical metallic cell.

9. The method of claim 1, wherein the hydrocarbon fluid is injected in the test cell at a constant flow rate.

10. The method of claim 1, further comprising measuring initial conductivity of the damaged sample to a gas flow using a non-reactive gas.

11. The method of claim 10, wherein the non-reactive gas is nitrogen.

12. The method of claim 1, wherein the evolution of the differential pressure (ΔP) is monitored.

13. The method of claim 1, wherein, an increase in differential pressure ΔP, is an indication that the micro-annulus or crack/fissure size has reduced and that the set cement system has reacted with the gas and shows self-healing properties.

14. A method of characterizing the self-healing properties of a set cement based material in contact with hydrocarbons in an oil or gas well or both, comprising:
   providing a test cell;
   providing said test cell with a sample of the set cement based material;
   damaging the sample to create a micro-annulus to the set cement;
   injecting a hydrocarbon fluid in the test cell;
   allowing the cement based material to heal by itself;
   measuring the differential pressure (ΔP) across the sample; and
   characterizing the self-healing properties of the cement based material from the measure of said differential pressure (ΔP).

15. The method of claim 14, wherein the test cell is a substantially cylindrical metallic cell.

16. The method of claim 14 further comprising measuring initial conductivity of the damaged sample to a gas flow using a non-reactive gas.

17. The method of claim 14, wherein the evolution of the differential pressure (ΔP) is monitored.

18. A method of characterizing the self-healing properties of a set cement based material in contact with hydrocarbons in an oil or gas well or both, comprising:
   providing a test cell;
   providing said test cell with a sample of the set cement based material;
   damaging the sample to create a micro-annulus, cracks or fissures to the set cement;
   injecting a hydrocarbon fluid in the test cell;
   allowing the cement based material to heal by itself;
   monitoring the evolution of the differential pressure (ΔP) across the sample; and
   characterizing the self-healing properties of the cement based material from said evolution of differential pressure (ΔP).

19. The method of claim 18, wherein the test cell is a substantially cylindrical metallic cell.

20. The method of claim 18 further comprising measuring initial conductivity of the damaged sample to a gas flow using a non-reactive gas.

* * * * *

UNITED STATES PATENT AND TRADEMARK OFFICE
CERTIFICATE OF CORRECTION

| | | |
|---|---|---|
| PATENT NO. | : 8,236,100 B2 | Page 1 of 1 |
| APPLICATION NO. | : 12/913761 | |
| DATED | : August 7, 2012 | |
| INVENTOR(S) | : Sylvaine Le Roy-Delage et al. | |

It is certified that error appears in the above-identified patent and that said Letters Patent is hereby corrected as shown below:

Title page, item [75] inventors:

They should be
2nd inventor: Helene Bulte-Loyer
4th inventor: Helene Heurdier

Signed and Sealed this
Eighteenth Day of September, 2012

David J. Kappos
*Director of the United States Patent and Trademark Office*